(12) United States Patent
Erickson et al.

(10) Patent No.: US 11,134,988 B2
(45) Date of Patent: Oct. 5, 2021

(54) ANKLE FIXATION SYSTEM

(71) Applicants: Nathan Erickson, Beaver Dam, UT (US); Nathan Plowman, Warsaw, IN (US); Neil Etherington, Warsaw, IN (US); Andrew R. Fauth, River Heights, UT (US); Jason W. Nascone, Highland, MD (US); Robert O'Toole, Lutherville, MD (US); Thomas Myers, Warsaw, IN (US); Russell M. Parrott, Warsaw, IN (US)

(72) Inventors: Nathan Erickson, Beaver Dam, UT (US); Nathan Plowman, Warsaw, IN (US); Neil Etherington, Warsaw, IN (US); Andrew R. Fauth, River Heights, UT (US); Jason W. Nascone, Highland, MD (US); Robert O'Toole, Lutherville, MD (US); Thomas Myers, Warsaw, IN (US); Russell M. Parrott, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 16/598,043

(22) Filed: Oct. 10, 2019

(65) Prior Publication Data
US 2020/0038062 A1 Feb. 6, 2020

Related U.S. Application Data

(63) Continuation of application No. 15/180,946, filed on Jun. 13, 2016, now abandoned.
(Continued)

(51) Int. Cl.
*A61B 17/64* (2006.01)

(52) U.S. Cl.
CPC ........ *A61B 17/6416* (2013.01); *A61B 17/645* (2013.01); *A61B 17/6425* (2013.01); *A61B 17/6441* (2013.01); *A61B 17/6458* (2013.01)

(58) Field of Classification Search
CPC ................ A61B 17/64; A61B 17/6491; Y10T 403/32639
See application file for complete search history.

(56) References Cited

U.S. PATENT DOCUMENTS

| | | |
|---|---|---|
| 2,238,870 A | 4/1941 | Haynes |
| 2,393,831 A | 1/1946 | Stader |

(Continued)

FOREIGN PATENT DOCUMENTS

| | | |
|---|---|---|
| CN | 2271351 | 12/1997 |
| CN | 1169279 A | 1/1998 |

(Continued)

OTHER PUBLICATIONS

US 6,030,385 A, 02/2000, Faccioli et al. (withdrawn)
(Continued)

*Primary Examiner* — Jan Christopher L Merene
(74) *Attorney, Agent, or Firm* — Schwegman Lundberg & Woessner, P.A.

(57) ABSTRACT

In an example, a clamping assembly includes a longitudinal member having a first end and a second end, the second end defining a first clamp, a second clamp configured to attach to the first end of the longitudinal member and connect to a rod assembly, a clamping member including a first end, a second end defining a spherical portion, and a third clamp, where the first clamp of the longitudinal member is configured to receive the second end of the clamping member.

19 Claims, 6 Drawing Sheets

Related U.S. Application Data (60) Provisional application No. 62/180,758, filed on Jun. 17, 2015.

(56) References Cited

U.S. PATENT DOCUMENTS

| | | |
|---|---|---|
| 4,135,505 A | 1/1979 | Day |
| 4,273,116 A | 6/1981 | Chiquet |
| 4,600,000 A | 7/1986 | Edwards et al. |
| 4,717,076 A | 1/1988 | Notkin |
| 4,745,913 A | 5/1988 | Castaman et al. |
| 5,207,676 A | 5/1993 | Canadell et al. |
| 5,275,599 A | 1/1994 | Zbikowski et al. |
| 5,314,426 A | 5/1994 | Pohl et al. |
| 5,356,421 A | 10/1994 | Castro |
| 5,376,090 A | 12/1994 | Pennig |
| 5,380,322 A | 1/1995 | Van Den Brink et al. |
| 5,403,313 A | 4/1995 | Lin |
| 5,439,465 A | 8/1995 | Tumibay |
| 5,443,464 A | 8/1995 | Russell et al. |
| 5,451,226 A | 9/1995 | Pfeil et al. |
| 5,454,810 A | 10/1995 | Pohl et al. |
| 5,591,164 A | 1/1997 | Nazre et al. |
| 5,658,283 A | 8/1997 | Huebner |
| 5,660,363 A | 8/1997 | Maglica |
| 5,672,175 A | 9/1997 | Martin |
| 5,688,271 A | 11/1997 | Faccioli et al. |
| 5,702,389 A | 12/1997 | Taylor et al. |
| 5,738,684 A | 4/1998 | Thomas et al. |
| 5,741,252 A | 4/1998 | Mazzio et al. |
| 5,766,173 A | 6/1998 | Ross, Jr. et al. |
| 5,769,851 A | 6/1998 | Veith |
| 5,891,144 A | 4/1999 | Mata et al. |
| 5,921,985 A | 7/1999 | Ross, Jr. et al. |
| 5,941,877 A | 8/1999 | Viegas et al. |
| 5,951,556 A | 9/1999 | Faccioli et al. |
| 5,961,515 A | 10/1999 | Taylor et al. |
| 5,976,136 A | 11/1999 | Bailey et al. |
| 6,010,501 A | 1/2000 | Raskin et al. |
| 6,080,153 A | 6/2000 | Mata et al. |
| 6,102,911 A | 8/2000 | Faccioli et al. |
| 6,162,224 A | 12/2000 | Huebner et al. |
| 6,171,308 B1 | 1/2001 | Bailey et al. |
| 6,176,860 B1 | 1/2001 | Howard |
| 6,176,881 B1 | 1/2001 | Schar et al. |
| 6,203,548 B1 | 3/2001 | Helland |
| 6,221,072 B1 | 4/2001 | Termaten |
| 6,235,029 B1 | 5/2001 | Faccioli et al. |
| 6,245,071 B1 | 6/2001 | Pierson |
| 6,277,118 B1 | 8/2001 | Grant et al. |
| 6,328,737 B1 | 12/2001 | Moorcroft et al. |
| 6,409,729 B1 | 6/2002 | Martinelli et al. |
| 6,428,540 B1 | 8/2002 | Claes et al. |
| 6,482,206 B2 | 11/2002 | Schoenefeld |
| 6,500,177 B1 | 12/2002 | Martinelli et al. |
| 6,520,961 B1 | 2/2003 | Marsh |
| 6,530,925 B2 | 3/2003 | Boudard et al. |
| 6,569,164 B1 | 5/2003 | Assaker et al. |
| 6,578,801 B2 | 6/2003 | Attee |
| 6,613,049 B2 | 9/2003 | Winquist et al. |
| 6,652,523 B1 | 11/2003 | Evrard et al. |
| 6,702,814 B2 | 3/2004 | Walulik et al. |
| 6,793,655 B2 | 9/2004 | Orsak |
| 6,840,939 B2 | 1/2005 | Venturini et al. |
| 6,860,883 B2 | 3/2005 | Janowski et al. |
| 6,913,587 B2 | 7/2005 | Slishman et al. |
| 6,988,696 B2 | 1/2006 | Attee et al. |
| 7,048,735 B2 | 5/2006 | Ferrante et al. |
| 7,147,639 B2 | 12/2006 | Berki et al. |
| 7,241,074 B2 | 7/2007 | Thomke et al. |
| 7,261,713 B2 | 8/2007 | Langmaid et al. |
| 7,282,052 B2 | 10/2007 | Mullaney |
| 7,306,601 B2 | 12/2007 | Mcgrath et al. |
| 7,311,711 B2 | 12/2007 | Cole |
| 7,320,555 B2 | 1/2008 | Chang et al. |
| 7,749,224 B2 | 7/2010 | Cresina et al. |
| 7,875,030 B2 | 1/2011 | Hoffmann-Clair |
| 7,931,650 B2 | 4/2011 | Winquist et al. |
| 8,029,546 B2 | 10/2011 | Capote |
| 8,057,474 B2 | 11/2011 | Knuchel et al. |
| 8,147,490 B2 | 4/2012 | Bauer |
| 8,157,295 B2 | 4/2012 | Krywitsky |
| 8,206,418 B2 | 6/2012 | Triplett et al. |
| 8,262,656 B2 | 9/2012 | Mirza et al. |
| 8,303,587 B2 | 11/2012 | Lehmann et al. |
| 8,323,281 B2 | 12/2012 | Hotchkiss et al. |
| 8,343,166 B2 | 1/2013 | Maughan et al. |
| 8,425,512 B2 | 4/2013 | Vasta et al. |
| 8,540,713 B2 | 9/2013 | Zandona et al. |
| 8,672,978 B2 | 3/2014 | Dant et al. |
| 8,734,446 B2 | 5/2014 | Miller |
| 9,301,782 B2 | 4/2016 | Myers et al. |
| 9,918,748 B2 | 3/2018 | Kalfas et al. |
| 9,924,969 B2 | 3/2018 | Triplett |
| 9,962,187 B2 | 5/2018 | Erickson |
| 10,010,348 B2 | 7/2018 | Myers et al. |
| 10,433,873 B2 | 10/2019 | Myers et al. |
| 10,543,019 B2 | 1/2020 | Erickson |
| 10,905,469 B2 | 2/2021 | Triplett et al. |
| 2004/0059331 A1 | 3/2004 | Mullaney |
| 2004/0133199 A1 | 7/2004 | Coati et al. |
| 2005/0131409 A1 | 6/2005 | Chervitz et al. |
| 2006/0155276 A1 | 7/2006 | Walulik et al. |
| 2006/0229602 A1 | 10/2006 | Olsen et al. |
| 2006/0287652 A1 | 12/2006 | Lessig et al. |
| 2007/0086849 A1 | 4/2007 | Chang et al. |
| 2007/0123856 A1 | 5/2007 | Deffenbaugh et al. |
| 2009/0036892 A1 | 2/2009 | Karidis et al. |
| 2009/0118733 A1 | 5/2009 | Orsak et al. |
| 2009/0228006 A1 | 9/2009 | Mussolin |
| 2009/0299368 A1 | 12/2009 | Bauer et al. |
| 2009/0306499 A1 | 12/2009 | Van Vorhis et al. |
| 2010/0249779 A1 | 9/2010 | Hotchkiss et al. |
| 2010/0312243 A1 | 12/2010 | Ross et al. |
| 2010/0331840 A1 | 12/2010 | Ross et al. |
| 2011/0098707 A1 | 4/2011 | Mullaney |
| 2011/0172665 A1 | 7/2011 | Winquist et al. |
| 2011/0245830 A1 | 10/2011 | Zgonis et al. |
| 2012/0150186 A1 | 6/2012 | Hajianpour |
| 2012/0253410 A1 | 10/2012 | Taylor et al. |
| 2012/0303029 A1 | 11/2012 | Vasta et al. |
| 2012/0303032 A1 | 11/2012 | Mirza et al. |
| 2013/0110110 A1 | 5/2013 | Waisman |
| 2013/0274807 A1 | 10/2013 | Prajapati |
| 2013/0296857 A1 | 11/2013 | Barnett et al. |
| 2014/0066931 A1 | 3/2014 | Myers et al. |
| 2014/0088649 A1 | 3/2014 | Refai |
| 2014/0316468 A1 | 10/2014 | Keiser et al. |
| 2014/0350558 A1 | 11/2014 | Triplett et al. |
| 2015/0100089 A1 | 4/2015 | Richelsoph et al. |
| 2015/0282842 A1 | 10/2015 | Beyar et al. |
| 2015/0337890 A1 | 11/2015 | Faccioli et al. |
| 2016/0038184 A1 | 2/2016 | Erickson |
| 2016/0199099 A1 | 7/2016 | Myers et al. |
| 2016/0367291 A1 | 12/2016 | Erickson et al. |
| 2018/0098792 A1 | 4/2018 | Triplett et al. |
| 2018/0161066 A1 | 6/2018 | Erickson |
| 2018/0271561 A1 | 9/2018 | Myers et al. |

FOREIGN PATENT DOCUMENTS

| | | |
|---|---|---|
| CN | 1494397 A | 5/2004 |
| CN | 101184447 A | 5/2008 |
| CN | 102018557 | 4/2011 |
| CN | 102292042 | 12/2011 |
| CN | 102368981 A | 3/2012 |
| CN | 202933000 U | 5/2013 |
| CN | 104619276 A | 5/2015 |
| CN | 104619276 B | 8/2016 |
| CN | 106794034 A | 5/2017 |
| CN | 107645936 A | 1/2018 |
| EP | 0639352 A1 | 2/1995 |
| EP | 0807419 A2 | 11/1997 |
| EP | 1238636 A1 | 9/2002 |
| FR | 2520607 A3 | 8/1983 |

(56) References Cited

FOREIGN PATENT DOCUMENTS

| | | |
|---|---|---|
| JP | 2004350774 A | 12/2004 |
| JP | 2006507041 A | 3/2006 |
| JP | 2011502028 A | 1/2011 |
| JP | 2017523864 A | 8/2017 |
| JP | 2018509247 A | 4/2018 |
| WO | WO-9427514 A1 | 12/1994 |
| WO | WO-9516401 A1 | 6/1995 |
| WO | WO-2006126167 A2 | 11/2006 |
| WO | WO-2012122317 A2 | 9/2012 |
| WO | WO-2014039205 A1 | 3/2014 |
| WO | WO-2014146765 A1 | 9/2014 |
| WO | WO-2016025375 A1 | 2/2016 |
| WO | WO-2016154107 A1 | 9/2016 |
| WO | WO-2016205128 A1 | 12/2016 |
| WO | WO-2016205128 A2 | 12/2016 |
| WO | WO-2016205128 A3 | 12/2016 |

OTHER PUBLICATIONS

U.S. Appl. No. 13/961,729 U.S. Pat. No. 9,301,782, filed Aug. 7, 2013, External Fixation.
U.S. Appl. No. 15/073,264 U.S. Pat. No. 10,010,348, filed Mar. 17, 2016, External Fixation.
U.S. Appl. No. 15/995,538 U.S. Pat. No. 10,433,873, filed Jun. 1, 2018, External Fixation.
U.S. Appl. No. 14/456,407 U.S. Pat. No. 9,924,969, filed Aug. 11, 2014, External Fixation.
U.S. Appl. No. 15/839,459, filed Dec. 12, 2017, External Fixation.
U.S. Appl. No. 15/892,704 U.S. Pat. No. 10,543,019, filed Feb. 9, 2018, External Fixation.
U.S. Appl. No. 14/668,282 U.S. Pat. No. 9,962,187, filed Mar. 15, 2015, External Fixation.
U.S. Appl. No. 15/180,946, filed Jun. 13, 2016, Ankle Fixation System.
"U.S. Appl. No. 13/961,729, Final Office Action dated Sep. 30, 2015", 13 pgs.
"U.S. Appl. No. 13/961,729, Non Final Office Action dated May 15, 2015", 13 pgs.
"U.S. Appl. No. 13/961,729, Notice of Allowance dated Nov. 24, 2015", 5 pgs.
"U.S. Appl. No. 13/961,729, Response filed Apr. 24, 2015 to Restriction Requirement dated Mar. 19, 2015", 6 pgs.
"U.S. Appl. No. 13/961,729, Response filed Jul. 1, 2015 to Non Final Office Action dated May 15, 2015", 12 pgs.
"U.S. Appl. No. 13/961,729, Response filed Nov. 14, 2015 to Final Office Aciton dated Sep. 30, 2015", 10 pgs.
"U.S. Appl. No. 13/961,729, Restriction Requirement dated Mar. 19, 2015", 8 pgs.
"U.S. Appl. No. 14/456,407, Advisory Action dated Feb. 9, 2017", 3 pgs.
"U.S. Appl. No. 14/456,407, Corrected Notice of Allowance dated Feb. 27, 2018", 4 pgs.
"U.S. Appl. No. 14/456,407, Final Office Action dated Oct. 28, 2016", 11 pgs.
"U.S. Appl. No. 14/456,407, Non Final Office Action dated Apr. 28, 2016", 10 pgs.
"U.S. Appl. No. 14/456,407, Non Final Office Action dated Jun. 13, 2017", 11 pgs.
"U.S. Appl. No. 14/456,407, Notice of Allowance dated Sep. 29, 2017", 8 pgs.
"U.S. Appl. No. 14/456,407, Notice of Allowance dated Nov. 8, 2017", 9 pgs.
"U.S. Appl. No. 14/456,407, Response filed Jan. 27, 2017 to Final Office Action dated Oct. 28, 2016", 9 pgs.
"U.S. Appl. No. 14/456,407, Response filed Apr. 11, 2016 to Restriction Requirement dated Feb. 19, 2016", 9 pgs.
"U.S. Appl. No. 14/456,407, Response filed Jul. 28, 2016 to Non Final Office Action dated Apr. 28, 2016", 9 pgs.
"U.S. Appl. No. 14/456,407, Response filed Aug. 30, 2017 to Non Final Office Action dated Jul. 13, 2017", 8 pgs.
"U.S. Appl. No. 14/456,407, Restriction Requirement dated Feb. 19, 2016", 7 pgs.
"U.S. Appl. No. 14/668,282, Corrected Notice of Allowance dated Mar. 30, 2018", 2 pgs.
"U.S. Appl. No. 14/668,282, Final Office Action dated Jun. 1, 17", 21 pgs.
"U.S. Appl. No. 14/668,282, Non Final Office Action dated Nov. 15, 2016", 16 pgs.
"U.S. Appl. No. 14/668,282, Notice of Allowance dated Aug. 16, 2017", 8 pgs.
"U.S. Appl. No. 14/668,282, Notice of Allowance dated Dec. 18, 2017", 7 pgs.
"U.S. Appl. No. 14/668,282, Preliminary Amendment filed May 5, 2015", 3 pgs.
"U.S. Appl. No. 14/668,282, Response filed Feb. 15, 2017 to Non Final Office Action dated Nov. 15, 2016", 11 pgs.
"U.S. Appl. No. 14/668,282, Response filed Jul. 26, 2017 to Final Office Action dated Jun. 1, 2017", 8 pgs.
"U.S. Appl. No. 14/668,282, Response filed Oct. 31, 2016 to Restriction Requirement dated Sep. 15, 2016", 9 pgs.
"U.S. Appl. No. 14/668,282, Restriction Requirement dated Sep. 15, 2016", 8 pgs.
"U.S. Appl. No. 15/073,264, Amendment Under 37 C.F.R. § 1.312", 7 pgs.
"U.S. Appl. No. 15/073,264, Non Final Office Action dated Oct. 2, 2017", 13 pgs.
"U.S. Appl. No. 15/073,264, Notice of Allowance dated Feb. 27, 2018", 9 pgs.
"U.S. Appl. No. 15/073,264, Preliminary Amendment filed Mar. 17, 2016", 3 pgs.
"U.S. Appl. No. 15/073,264, PTO Response to Rule 312 Communication dated Jun. 5, 2018", 2 pgs.
"U.S. Appl. No. 15/073,264, Response filed Jul. 14, 2017 to Restriction Requirement dated Jan. 14, 2017", 7 pgs.
"U.S. Appl. No. 15/073,264, Response filed Dec. 19, 2017 to Non Final Office Action dated Oct. 2, 2017", 10 pgs.
"U.S. Appl. No. 15/073,264, Restriction Requirement dated Jun. 14, 2017", 6 pgs.
"U.S. Appl. No. 15/180,946, Non Final Office Action dated Apr. 17, 2018", 12 pgs.
"U.S. Appl. No. 15/180,946, Non Final Office Action dated Nov. 21, 2018", 15 pgs.
"U.S. Appl. No. 15/180,946, Notice of Allowance dated Mar. 13, 2019", 9 pgs.
"U.S. Appl. No. 15/180,946, Notice of Allowance dated Jul. 10, 2019", 9 pgs.
"U.S. Appl. No. 15/180,946, Respone filed Feb. 1, 2019 to Non Final Office Action dated Nov. 21, 2018", 9 pgs.
"U.S. Appl. No. 15/180,946, Response filed Jan. 11, 2018 to Restriction Requirement dated Dec. 13, 2017", 9 pgs.
"U.S. Appl. No. 15/180,946, Response filed Jun. 8, 2018 to Non Final Office Action dated Apr. 17, 2018", 13 pgs.
"U.S. Appl. No. 15/180,946, Restriction Requirement dated Dec. 13, 2017", 8 pgs.
"U.S. Appl. No. 15/839,459, Final Office Action dated Mar. 16, 2020", 6 pgs.
"U.S. Appl. No. 15/839,459, Non Final Office Action dated Oct. 31, 2019", 8 pgs.
"U.S. Appl. No. 15/839,459, Notice of Allowance dated Sep. 11, 2020", 12 pgs.
"U.S. Appl. No. 15/839,459, Notice of Allowance dated Sep. 23, 2020", 5 pgs.
"U.S. Appl. No. 15/839,459, Preliminary Amendment filed Dec. 13, 2017", 42 pgs.
"U.S. Appl. No. 15/839,459, Response filed Jan. 31, 2020 to Non Final Office Action dated Oct. 31, 2019", 9 pgs.
"U.S. Appl. No. 15/839,459, Response filed Sep. 25, 2019 to Restriction Requirement dated Jul. 25, 2019", 9 pgs.
"U.S. Appl. No. 15/839,459, Restriction Requirement dated Jul. 25, 2019", 7 pgs.

(56) References Cited

OTHER PUBLICATIONS

"U.S. Appl. No. 15/839,459, Supplemental Preliminary Amendment filed Dec. 19, 2017", 6 pgs.
"U.S. Appl. No. 15/892,704, Corrected Notice of Allowability dated Dec. 27, 2019", 5 pgs.
"U.S. Appl. No. 15/892,704, Final Office Action dated Jun. 20, 2019", 12 pgs.
"U.S. Appl. No. 15/892,704, Non Final Office Action dated Mar. 7, 2019", 11 pgs.
"U.S. Appl. No. 15/892,704, Notice of Allowance dated Dec. 16, 2019", 6 pgs.
"U.S. Appl. No. 15/892,704, Preliminary Amendment filed Feb. 13, 2018", 6 pgs.
"U.S. Appl. No. 15/892,704, Response filed Jun. 7, 2019 to Non-Final Office Action dated Mar. 7, 2019", 12 pgs.
"U.S. Appl. No. 15/892,704, Response filed Aug. 19, 2019 to Final Office Action dated Jun. 20, 2019", 11 pgs.
"U.S. Appl. No. 15/995,538, Examiner Interview Summary dated May 10, 2019", 3 pgs.
"U.S. Appl. No. 15/995,538, Final Office Action dated Mar. 29, 2019", 12 pgs.
"U.S. Appl. No. 15/995,538, Non Final Office Action dated Oct. 1, 2018", 14 pgs.
"U.S. Appl. No. 15/995,538, Notice of Allowance dated May 29, 2019", 7 pgs.
"U.S. Appl. No. 15/995,538, Response filed May 13, 2019 to Final Office Action dated Mar. 29, 2019", 9 pgs.
"U.S. Appl. No. 15/995,538, Response filed Dec. 19, 2018 to Non Final Office Action dated Oct. 1, 2018", 11 pgs.
"Application Serial No. PCT/US2016/023400, Invitation to Pay Additional Fees and Partial Search Report dated May 27, 2016", 7 pgs.
"Australian Application Serial No. 2015302014, First Examination Report dated Mar. 26, 2019", 5 pgs.
"Australian Application Serial No. 2015302014, Response filed May 24, 2019 to First Examination Report dated Mar. 26, 2018", 15 pgs.
"Australian Application Serial No. 2016235383, First Examination Report dated Jun. 6, 2019", 4 pgs.
"Australian Application Serial No. 2016235383, Response filed Aug. 13, 2019 to First Examination Report dated Jun. 6, 2019", 17 pgs.
"Canadian Application Serial No. 2,980,551, Office Action dated Feb. 20, 2020", 5 pgs.
"Canadian Application Serial No. 2,980,551, Response filed Jun. 19, 2020 to Office Action dated Feb. 20, 2020", 80 pgs.
"Chinese Application Serial No. 201380046175.X, Office Action dated Oct. 29, 2015", with English translation, 8 pages.
"Chinese Application Serial No. 201380046175.X, Response filed Feb. 24, 2016 to Office Action dated Oct. 29, 2015", with English claims, 8 pages.
"Chinese Application Serial No. 201580053427.0, Office Action dated Aug. 29, 2018", with English translation, 2 pages.
"Chinese Application Serial No. 201580053427.0, Office Action dated Nov. 5, 2018", with English translation, 12 pages.
"Chinese Application Serial No. 201580053427.0, Response filed Jan. 29, 2019 to Office Action dated Nov. 5, 2018", with English claims, 10 pages.
"Chinese Application Serial No. 201680030400.4, Office Action dated Jul. 22, 2020", with English translation, 15 pages.
"Chinese Application Serial No. 201680030400.4, Office Action dated Nov. 4, 2019", with English translation, 13 pages.
"Chinese Application Serial No. 201680030400.4, Response filed Feb. 26, 2020 to Office Action dated Nov. 4, 2019", with English claims, 8 pages.
"Chinese Application Serial No. 201680030400.4, Response filed Sep. 18, 2020 to Office Action dated Jul. 22, 2020", with English claims, 47 pages.

"European Application Serial No. 15751264.1, Response filed Oct. 9, 2017 to Office Action dated Mar. 28, 201717", 14 pgs.
"European Application Serial No. 16713258.8, Communication pursuant to Rule 164(2)(b) and Article 94(3) EPC dated Jun. 24, 2020", 10 pgs.
"European Application Serial No. 16713258.8, Response filed Aug. 30, 2018 to Office Action dated Jul. 25, 2018", 12 pgs.
"European Application Serial No. 16732138.9, Response filed Jul. 19, 2018 to Office Action dated Feb. 16, 2018", 14 pgs.
"International Application Serial No. PCT/US2013/054058, International Preliminary Report on Patentability dated Mar. 19, 2015", 7 pgs.
"International Application Serial No. PCT/US2013/054058, International Search Report dated Oct. 14, 2013", 4 pgs.
"International Application Serial No. PCT/US2015/044441, International Preliminary Report on Patentability dated Feb. 23, 2017", 12 pgs.
"International Application Serial No. PCT/US2015/044441, International Search Report dated Jan. 25, 2016", 6 pgs.
"International Application Serial No. PCT/US2015/044441, Invitation to Pay Additional Fees and Partial Search Report dated Oct. 22, 2015", 5 pgs.
"International Application Serial No. PCT/US2015/044441, Written Opinion dated Jan. 25, 2016", 10 pgs.
"International Application Serial No. PCT/US2016/023400, International Preliminary Report on Patentability dated Oct. 5, 2017", 10 pgs.
"International Application Serial No. PCT/US2016/023400, International Search Report dated Aug. 9, 2016", 6 pgs.
"International Application Serial No. PCT/US2016/023400, Written Opinion dated Aug. 9, 2016", 8 pgs.
"International Application Serial No. PCT/US2016/037228, International Preliminary Report on Patentability dated Dec. 28, 2017", 8 pgs.
"International Application Serial No. PCT/US2016/037228, International Search Report dated Feb. 14, 2017", 7 pgs.
"International Application Serial No. PCT/US2016/037228, Written Opinion dated Feb. 14, 2017", 6 pgs.
"Japanese Application Serial No. 2017-507855, Notification of Reasons for Refusal dated Mar. 31, 2020", with English translation, 4 pages.
"Japanese Application Serial No. 2017-507855, Notification of Reasons for Rejection dated Jul. 2, 2019", with English translation, 9 pages.
"Japanese Application Serial No. 2017-507855, Response filed Jun. 30, 2020 to Notification of Reasons for Refusal dated Mar. 31, 2020", with English claims, 11 pages.
"Japanese Application Serial No. 2017-507855, Response filed Oct. 2, 2019 to Notification of Reasons for Rejection dated Jul. 2, 2019", with English claims, 14 pages.
"Japanese Application Serial No. 2017-549753, Notification of Reasons for Rejection dated Feb. 4, 2020", with English translation, 9 pages.
Stryker, "Hoffman II MRI, External Fixation Systems Brochure", Literature No. 5075-1-600, LotD4508, Copyright 2008, 12 pgs.
Stryker, "Hoffmanxpress Brochure", Literature No. 982336, Lot B0409, Copyright 2009, 24 pgs.
"U.S. Appl. No. 15/839,459, Corrected Notice of Allowability dated Dec. 30, 2020", 4 pgs.
"European Application Serial No. 16713258.8, Response filed Nov. 4, 2020 to Communication pursuant to Rule 164(2)(b) and Article 94(3) EPC dated Jun. 24, 2020", 12 pgs.
"Japanese Application Serial No. 2017-507855, Office Action dated Nov. 10, 2020", with English translation, 4 pages.
"Chinese Application Serial No. 201680030400.4, Office Action dated Jan. 20, 2021", with English translation, 15 pages.
"Chinese Application Serial No. 201680030400.4, Response filed Mar. 12, 2021 to Office Action dated Jan. 20, 2021", with English claims, 8 pages.
"Japanese Application Serial No. 2017-507855, Response filed Mar. 9, 2021 to Office Action dated Nov. 10, 2020", with English claims, 17 pages.

ANKLE FIXATION SYSTEM

CLAIM OF PRIORITY

This application is a continuation of U.S. patent application Ser. No. 15/180,946, filed on Jun. 13, 2016, which claims the benefit of U.S. Provisional Patent Application Ser. No. 62/180,758, filed on Jun. 17, 2015, the benefit of priority of each of which is claimed hereby, and each of which is incorporated by reference herein in its entirety.

TECHNICAL HELD

This disclosure pertains generally, but not by way of limitation, to systems, devices and methods for external fixation of joints and/or fractured bones.

BACKGROUND

The systems, devices and methods described in this disclosure may be used for stabilization of a traumatic injury until a long-term stabilization device can be applied. Short-term or temporary stabilization may allow soft tissues to recover from trauma prior to definitive skeletal fixation; for example, reduction of swelling, healing of open wounds, and/or healing of skin abrasions prior to open reduction and internal fixation. External fixation may also be used when transportation is required from the site of initial care, such as a local or rural hospital to a secondary site with appropriate trauma capabilities, such as a regional trauma center. Short-term stabilization may also be used for injuries that occur during periods of time when appropriate trauma care is not available, such as after hours, until a skilled clinician becomes available. Short-term stabilization may be appropriate in battlefield or field hospital situations. There is a need for external fixation systems and methods which are simple, easy, and affordable.

OVERVIEW

In an example, this disclosure is directed to a clamping assembly comprising a longitudinal member having a first end and a second end, the second end defining a first clamp; a second clamp configured to attach to the first end of the longitudinal member and connect to a rod assembly; a clamping member including a first end, a second end defining a spherical portion, and a third clamp, wherein the first clamp of the longitudinal member is configured to receive the second end of the clamping member.

In another example, this disclosure is directed to a metatarsal bone pin clamping assembly comprising: a longitudinal member having a first end and a second end, the second end defining a first clamp, the first clamp including a spherical clamping surface; a U-shaped clamp configured to attach to the first end of the longitudinal member and connect to a rod assembly; a clamping member including a first end, a second end defining a spherical portion configured to expand, and a third clamp; a first fixation bolt extending through a portion of the clamping member and the spherical portion; a nut configured to receive an end of the first fixation bolt; and a first bone pin locking member including a spherical portion, wherein the first clamp of the longitudinal member is configured to receive the second end of the clamping member, wherein the spherical clamping surface of the first clamp is configured to receive the spherical portion and form a polyaxial joint between the clamping member and the longitudinal member, wherein the spherical portion is configured to expand when the first fixation bolt is turned and the nut is pulled into the spherical portion; and wherein the third clamp includes a spherical clamping surface configured to receive the spherical portion of the first bone pin locking member and form a polyaxial joint between the clamping member and a first bone pin.

In another example, this disclosure is directed to an external fixation system comprising: a first clamp assembly; a second clamp assembly; a rod assembly secured to and extending between the first clamp assembly and the second clamp assembly, the first rod assembly including a first tubular member and a second tubular member received in the first tubular member; and a bone pin clamping assembly comprising: a longitudinal member having a first end and a second end, the second end defining a first clamp; a second clamp configured to attach to the first end of the longitudinal member and connect to the rod assembly; a clamping member including a first end, a second end defining a spherical portion, and a third clamp, wherein the first clamp of the longitudinal member is configured to receive the second end of the clamping member.

In another example, this disclosure is directed to a method for external fixation of a limb, the limb having a first bone portion, the method comprising: securing a first bone pin to the first bone portion; attaching a pre-assembled external fixation system to the first bone pin; the external fixation system comprising a rod assembly; securing a second bone pin to a bone in a foot; attaching a clamping assembly to the rod assembly, the clamping assembly comprising: a longitudinal member having a first end and a second end, the second end defining a first clamp; a second clamp configured to attach to the first end of the longitudinal member and connect to the rod assembly; a clamping member including a first end, a second end defining a spherical portion, a bone pin locking member, and a third clamp configured to receive the bone pin locking member, wherein the first clamp of the longitudinal member is configured to receive the second end of the clamping member; aligning the bone pin locking member of the clamping assembly with the second bone pin; inserting the second bone pin into the bone pin locking member of the clamping assembly; and securing the bone pin locking member of the clamping assembly to the second bone pin.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
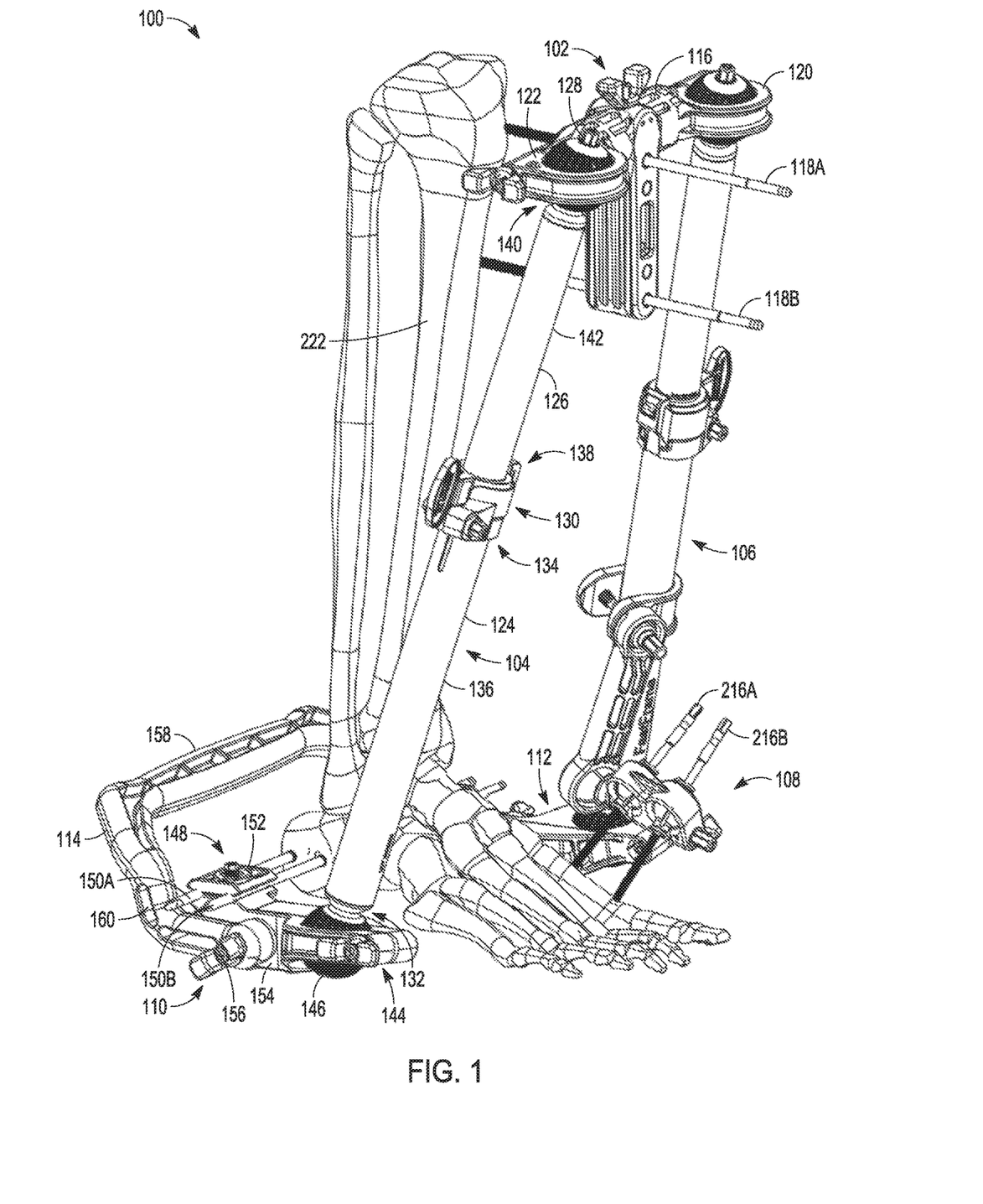
FIG. 1 is a perspective view of an external fixation system, secured to a tibia, a calcaneus, and a metatarsal, in accordance with this disclosure.

FIG. 1 is a perspective view of an external fixation system, in accordance with this disclosure. The external fixation system 100 of FIG. 1 can be configured to immobilize an ankle joint, for example. In the example configuration depicted in FIG. 1, the external fixation system 100 can include a clamp assembly 102, a first rod assembly 104, a second rod assembly 106, a bone pin clamping assembly 108, a first clamping strut assembly 110, a second clamping strut assembly 112, and a kickstand member 114.

The clamp assembly 102 of FIG. 1 can include a clamp body 116 configured to receive one or more bone pins 118A, 118B, and having a first clamp 120 and a second clamp 122. The first clamp 120 is configured to receive an end of the first rod assembly 104 and the second clamp 122 is configured to receive an end of the second rod assembly 106. An example clamp assembly 102 is described in detail in commonly assigned U.S. patent application Ser. No. 14/456,407, titled "External Fixation", to Triplett et al. and filed on Aug. 11, 2014, the entire content of which is incorporated herein by reference.

The first rod assembly 104 can include an outer or first tubular element 124, an inner or second tubular element 126, a locking screw 128, and a rod clamp assembly 130. The first tubular element 124 has a first end 132 and a second end 134 and shaft 136 extending therebetween. The second tubular element 126 has a first end 138 and a second end 140 and a shaft 142 extending therebetween. The first tubular element 124 is larger in diameter than and coaxially receives a portion of the second tubular element 126. The tubular elements may be circular in cross-section as shown, or, in other embodiments, may be square, rectangular, triangular, or any other polygonal shape in cross-section. The tubular elements may also be referred to as rods, rod elements, or rod members.

The second rod assembly 106 is substantially similar to the first rod assembly 104 and, for purposes of conciseness, will not be described separately.

Figure 7:
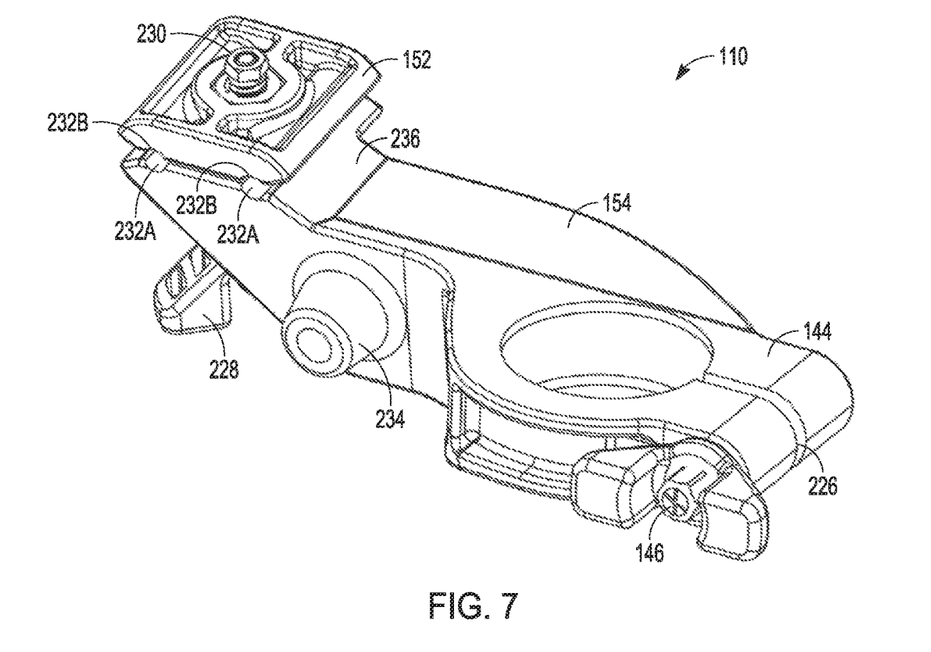
FIG. 7 is a perspective view of an example of a clamping strut assembly.

The first clamping strut assembly 110, shown in more detail in FIG. 7, can include a first clamp 144 configured to receive an end 132 of the first rod assembly 104. The first clamping strut assembly 110 can include a first fixation bolt 146 that, when tightened, securingly engages the end 132 of the first rod assembly 104. The first clamping strut assembly 110 can further include a second clamp 148 configured to securingly engage one or more bone pins 150A, 150B, e.g., calcaneal pins. As a fixation bolt is tightened (shown at 228 in FIG. 7), the bone pins 150A, 150B can be secured between a plate 152 and a body 154 of the first clamping strut assembly 110.

The second clamping strut assembly 112 is substantially similar to the first clamping strut assembly 110 and, for purposes of conciseness, will not be described separately.

The system 100 of FIG. 1 can further include a kickstand member 114. The kickstand member 114 can be affixed to the first clamping strut assembly 110 using a second fixation bolt 156 and to the second clamping strut assembly 112 using a third fixation bolt (not depicted in FIG. 1). When the second and third fixation bolts are loosened, the kickstand member 114 can be rotated behind the patient's heel (as shown in FIG. 1) or under the patient's foot (not depicted).

When the kickstand member 114 is rotated under the foot, a clinician, e.g., physician, can grip the kickstand member, e.g., at portion 158, and pull axially in order to get traction on the patient's ankle while setting the ankle fracture. When the kickstand member 114 is rotated behind the patient's ankle (as shown in FIG. 1), the patient's foot can be elevated to improve blood flow, for example.

In the example configuration shown in FIG. 1, the kickstand member 114 is not attached to the bone pins 150A, 150B extending into the patient's heel. Rather, the kickstand member 114 can include a portion 160 that can allow the member 114 to clear or avoid the bone pins 150A, 150B as the member 114 is rotated behind the heel.

As mentioned above, in some configurations, the system 100 can include the bone pin clamping assembly 108, which is shown and described in more detail below with respect to FIGS. 4, 5A, 5B, and 6. As described in more detail below, the bone pin clamping assembly 108 can provide a polyaxially rotating clamp, thereby providing increased range of motion and degrees of freedom over existing clamp design.

Advantageously, the increased range of motion and degrees of freedom provided by the bone pin clamping assembly 108 of this disclosure can eliminate the need for a spanning member that extends across a patient's foot, such as the spanning member 808 in FIG. 12 in commonly assigned U.S. patent application Ser. No. 13/961,729, titled "External Fixation", to Myers et al. and filed on Aug. 7, 2013, the entire content of which is incorporated herein by reference. The spanning member can obstruct a physician's view and can also interfere with the healing process, e.g., as the foot swells.

Figure 2:
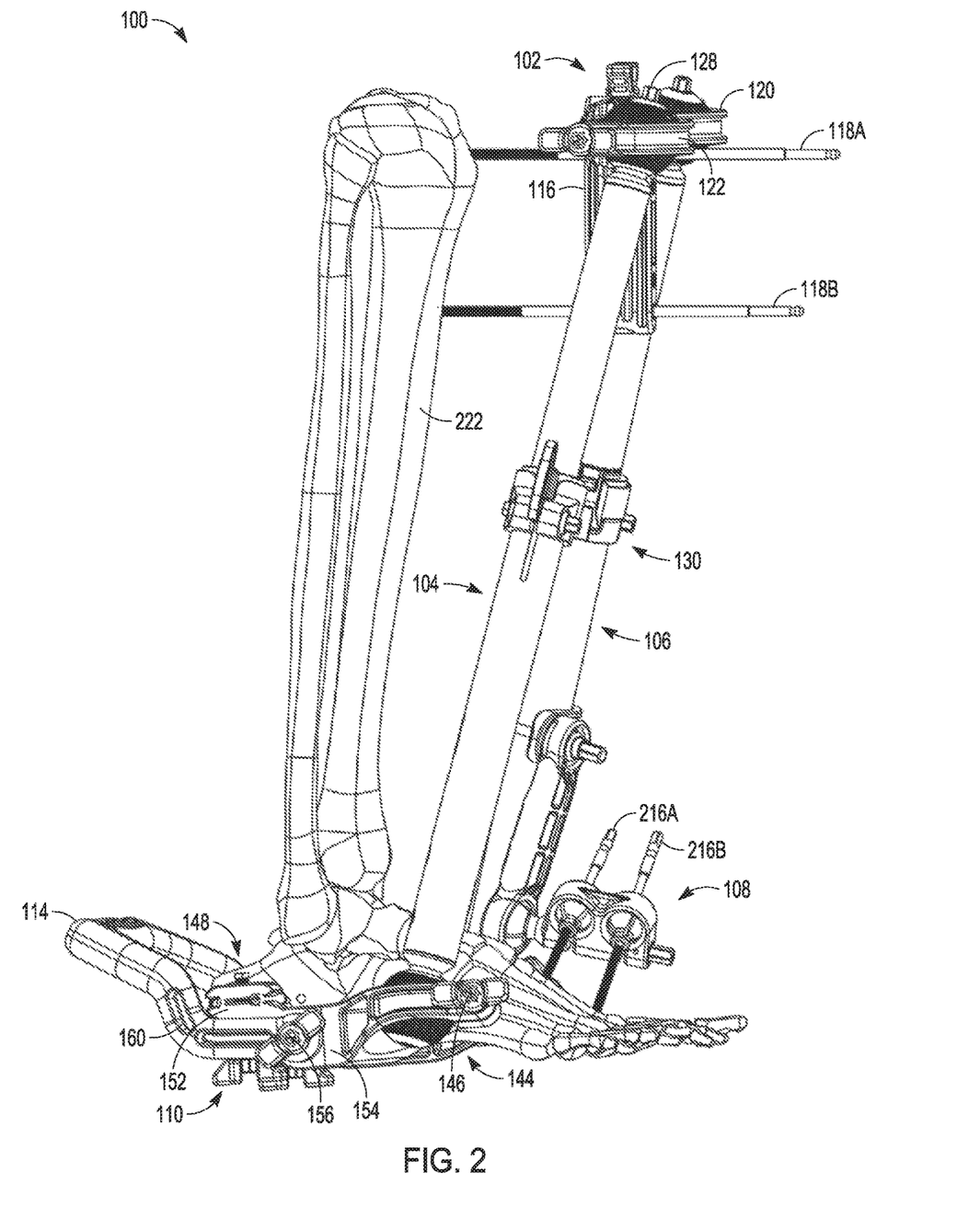
FIG. 2 is a side view of the external fixation system of FIG. 1, in accordance with this disclosure. For purposes of conciseness, FIG. 2 will not be described separately.

FIG. 2 is a side view of the external fixation system of FIG. 1, in accordance with this disclosure. For purposes of conciseness, FIG. 2 will not be described separately.

Figure 3:
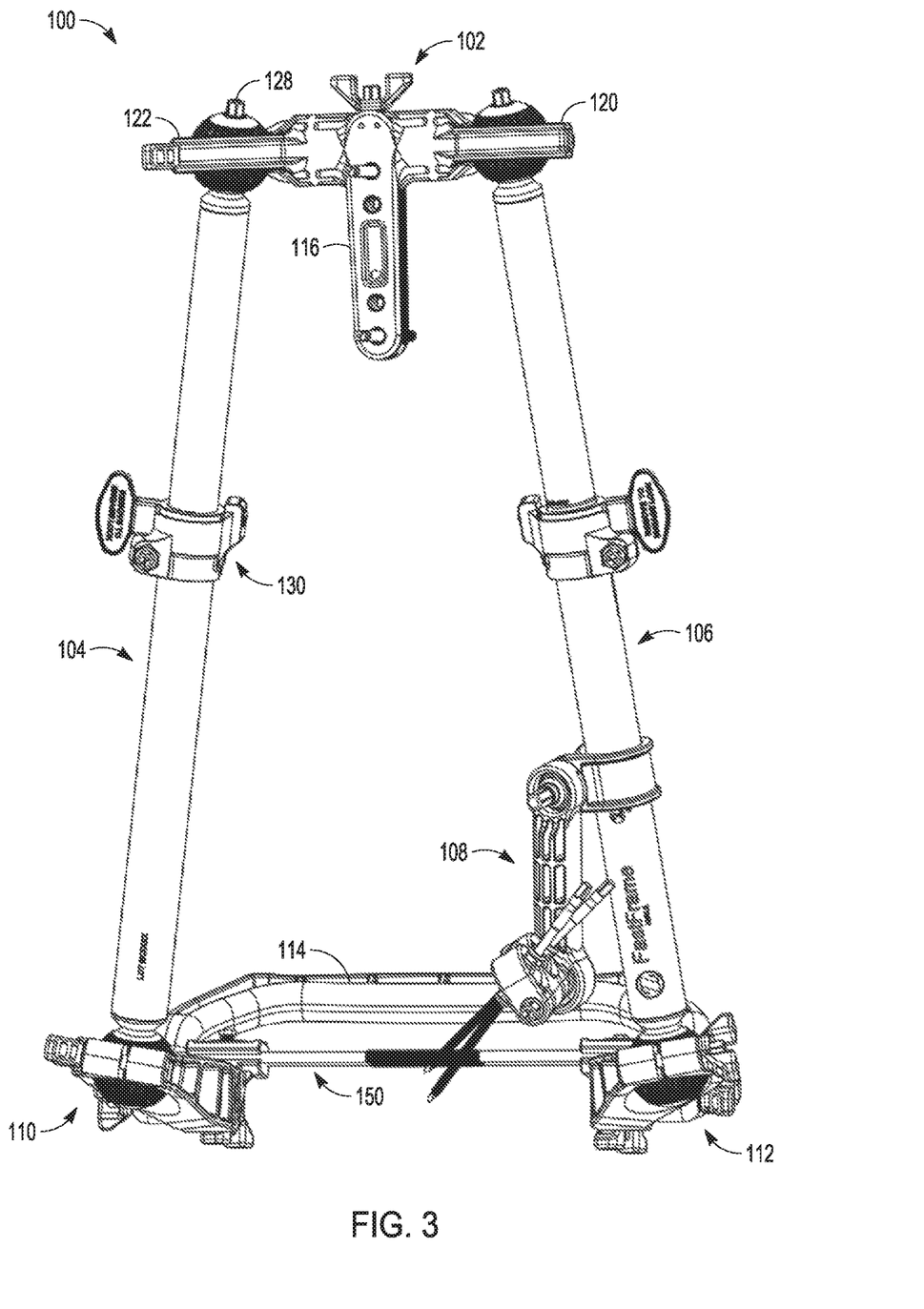
FIG. 3 is a side view of the external fixation system of FIGS. 1 and 2, in accordance with this disclosure. For purposes of conciseness, FIG. 3 will not be described separately.

FIG. 3 is a side view of the external fixation system of FIGS. 1 and 2, in accordance with this disclosure. For purposes of conciseness, FIG. 3 will not be described separately. It should be noted that the clamping assembly 108 of FIGS. 1-3 is optional.

Figure 4:
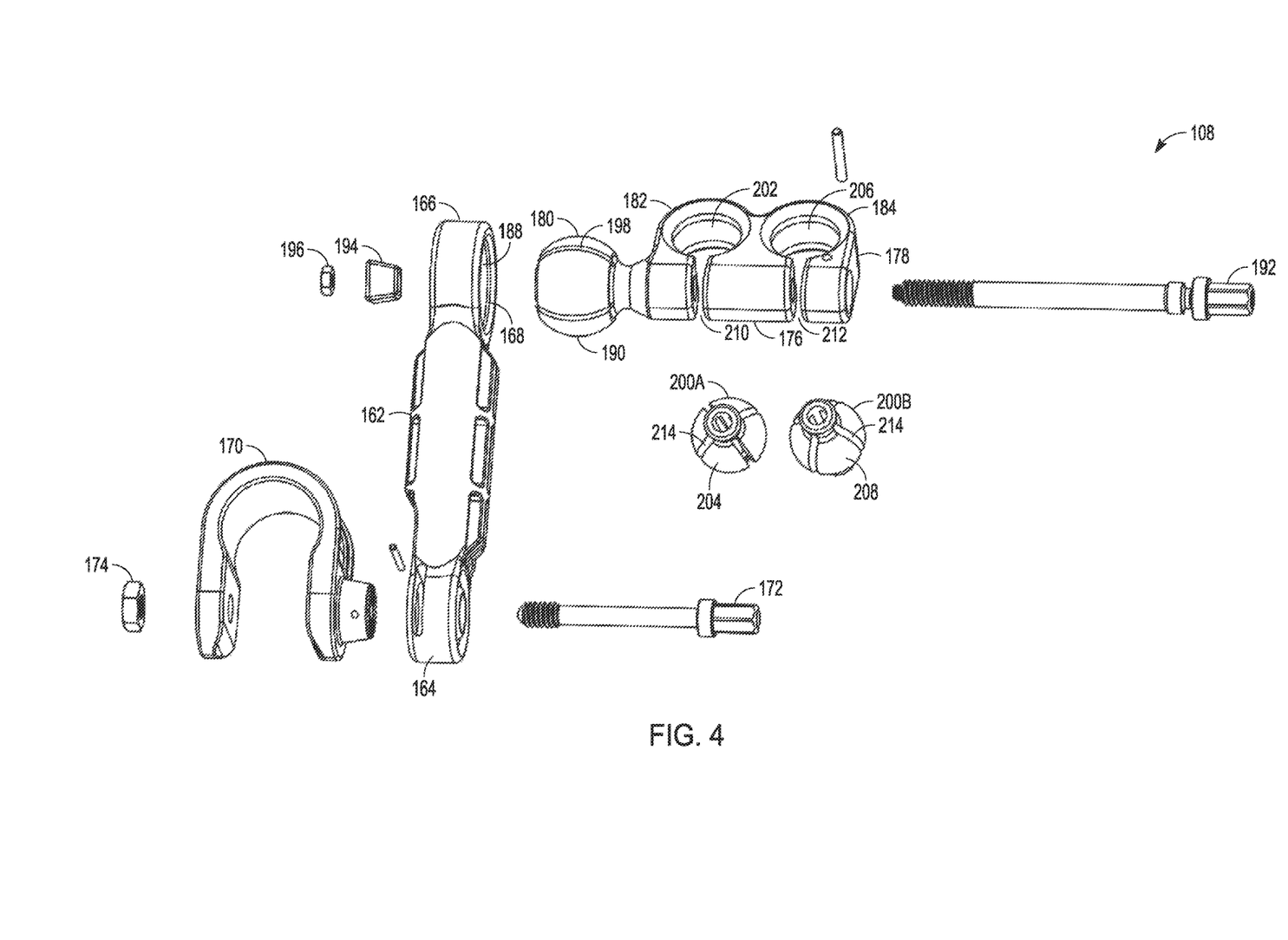
FIG. 4 is an exploded view of the clamping assembly 108 of the external fixation system of FIGS. 1-3.

FIG. 4 is an exploded view of the clamping assembly 108 of the external fixation system of FIGS. 1-3. The clamping assembly 108 can include a longitudinal member 162 having a first end 164 and a second end 166. As seen in FIG. 4, the second end 166 of the longitudinal member 162 can define a first clamp 168.

The clamping assembly 108 can include a second clamp 170 configured to attach to the first end 164 of the longitudinal member 162 and connect to a rod assembly, e.g., rod assembly 106 of FIG. 1, In some example configurations, the second clamp can be a U-shaped clamp.

In some example configurations, the second clamp 170 can be configured to frictionally engage a rod assembly, e.g., rod assembly 106 of FIG. 1. For example, the clamping assembly 108 can include a first fixation bolt 172 configured to extend through the first end 164 of the longitudinal member 162 and at least a portion of the second clamp 170. The first fixation bolt 172 can be secured using a nut 174, for example. When tightened, the first fixation bolt 172 can pull the sides of the second clamp 170 together, thereby securing the clamp 170 to the rod assembly 106.

The clamping assembly 108 can include a bone pin clamping member 176 including a first end 178, a second end 180 defining a spherical portion, and at least a third clamp 182. The third clamp 182 can be configured to receive a first bone pin, e.g., a metatarsal bone pin. The example configuration shown in FIG. 4 can include a fourth clamp 184 configured to receive a second bone pin, e.g., a metatarsal bone pin.

In some examples, the first clamp 168 of the longitudinal member 162 can include a spherical clamping surface 188 configured to receive the spherical portion of the second end 180 of the clamping member 176. The spherical clamping surface 188 can include an inner surface configured to substantially conform to an outer surface of the spherical portion. A spherical portion can include, for example, a sphere or a truncated sphere (e.g., a sphere in which two opposing portions are truncated by parallel planes), where at least some of the spherical portion retains a spherical shape. As described in more detail below, the spherical portion of the second end 180 of the clamping member 176 in combination with the first clamp 168 can provide a polyaxial joint between the longitudinal member 162 and the clamping member 176.

Figure 6:
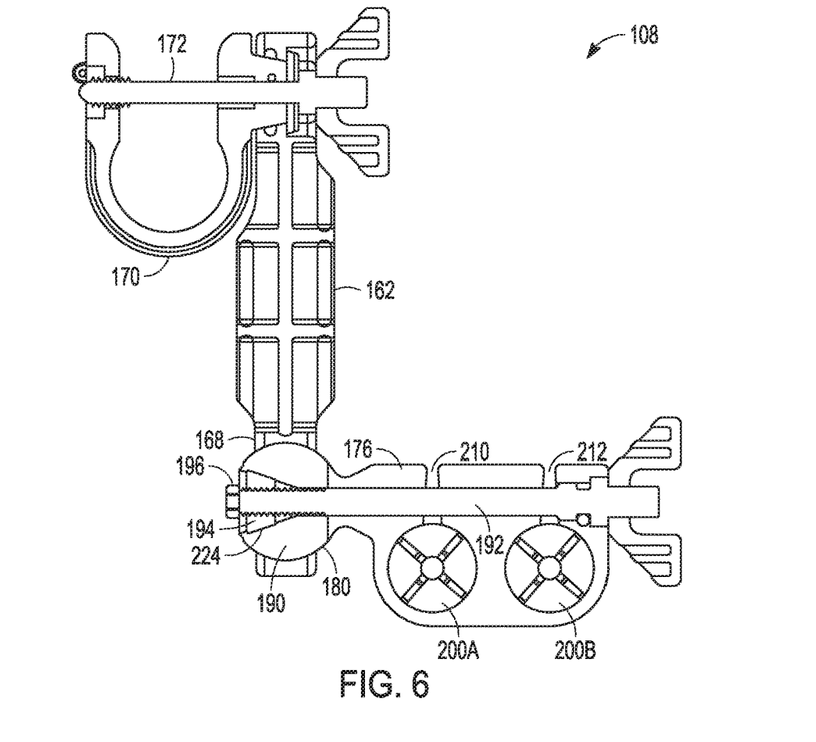
FIG. 6 is a cross-sectional view of the clamping assembly 108 of FIG. 1.

In an example configuration, the clamping member 176 and, in particular, the spherical portion 190 can be secured to the longitudinal member 162 using a second fixation bolt 192, In FIG. 4, the second fixation bolt 192 can extend through a portion of the clamping member 176. As shown in FIG. 6, the second fixation bolt 192 can extend into the spherical portion 190, which is configured to receive a first nut 194. As the second fixation bolt 192 is turned, the nut 194 is drawn into the spherical portion 190, causing the spherical portion 190 to expand against the inner surface of the first clamp 168. In the example shown in FIG. 4, the nut 194 can include tapered sides. The assembly 108 can include a second nut 196 to secure the fixation bolt 192. In some examples, the spherical portion 190 can define one or more slots 198, which can facilitate the expansion of the spherical portion 190.

The clamping assembly 108 can also include a first bone pin locking member 200A. In example configurations that include a fourth clamp 184, as shown in FIG. 4, the clamping assembly 108 can include a second bone pin locking member 200B. The first and the second bone pin locking members 200A, 200B are collectively referred to as "bone pin locking members 200" in this disclosure. The bone pin locking members 200 can be configured to receive respective bone pins, e.g., metatarsal bone pins (depicted in FIGS. 5A, 5B).

In the example shown in FIG. 4, the bone pin locking members 200 can include a spherical portion. The third clamp 182 can include a spherical clamping surface 202 configured to receive a spherical portion 204 of the first bone pin locking member 200A and form a polyaxial joint between the clamping member 176 and a first bone pin. The spherical portion 204 of the first bone pin locking member 200A can be configured to compress when the third clamp 182 contracts.

Similarly, the fourth clamp 184 can include a spherical clamping surface 206 configured to receive a spherical portion 208 of the second bone pin locking member 200B and form a polyaxial joint between the clamping member 176 and a second bone pin. The spherical portion 208 of the second bone pin locking member 200B can be configured to compress when the fourth clamp 184 contracts.

As seen in FIG. 4, the clamping member 176 can define a first gap 210 and a second gap 212. When the second fixation bolt 192 is turned and the nut 194 is pulled into the spherical portion 190 of the second end 180, the first gap 210 closes and the third clamp 182 contracts against the spherical portion 204 of the first bone pin locking member 200A. Similarly, in configurations including a fourth clamp (as shown in FIG. 4), when the second fixation bolt 192 is turned and the nut 194 is pulled into the spherical portion 190 of the second end 180, the second gap 212 closes and the fourth clamp 184 contracts against the spherical portion 190 of the second bone pin locking member 200B, causing the contraction of the spherical portion of the bone pin locking members 200. The bone pin locking members 200 contract against the bone pins extending through the bone pin locking members 200 (depicted in FIGS. 5A, 5B).

In some examples, the spherical portion of the bone pin locking members 200 can define one or more slots 214, which can facilitate the contraction of the spherical portion of the bone pin locking members 200.

Figure 5A:
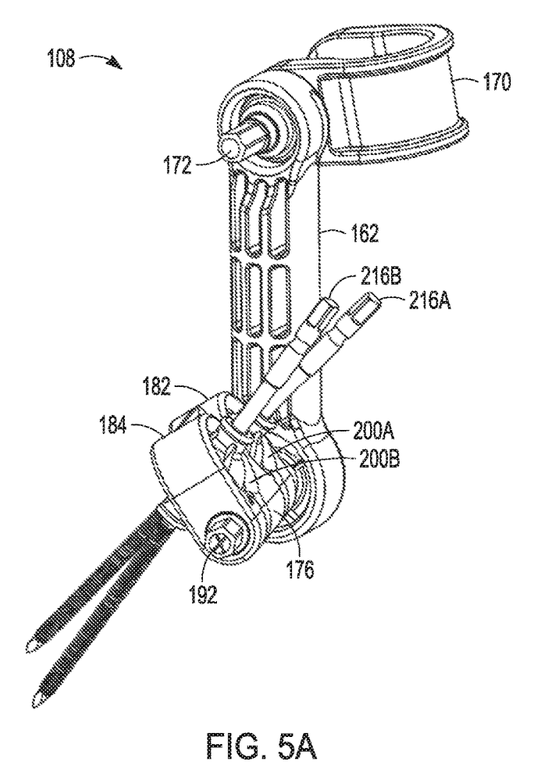
FIGS. 5A and 5B depict perspective views of the clamping assembly 108 of FIG. 1.
Figure 5B:
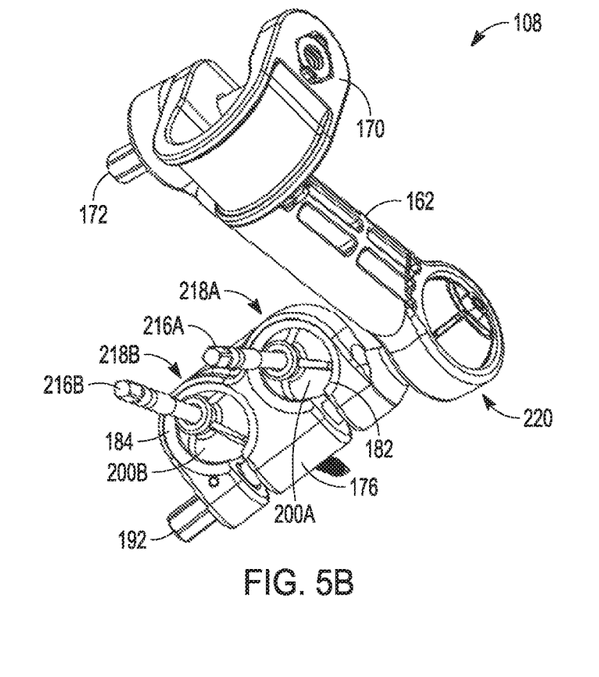

FIGS. 5A and 5B depict perspective views of the clamping assembly 108 of FIG. 1. For purposes of conciseness, FIGS. 5A and 5B will be described together.

The assembled clamping assembly 108 shown in FIGS. 5A and 5B depicts the first bone pin locking member 200A and the second bone pin locking member 200B securing, respectively, a first bone 216A and a second bone pin 216B (collectively referred to as bone pins 216 in this disclosure), within the third clamp 182 and the fourth clamp 184. As mentioned above, the third clamp 182 can include a spherical clamping surface configured to receive a spherical portion of the first bone pin locking member 200A and form a polyaxial joint 218A between the clamping member 176 and the first bone pin 200A, and, similarly, the fourth clamp 184 can include a spherical clamping surface configured to receive a spherical portion of the second bone pin locking member 200B and form a polyaxial joint 218B between the clamping member and a second bone pin 216B.

In some example implementations, the multiple polyaxial joints, e.g., joint 218A, joint 218B, and joint 220 best shown FIG. 5B, of the clamping assembly 108 can advantageously allow a physician, for example, to secure the first bone pin 216A and the second bone pin 216B into a patient's foot, e.g., a metatarsal, and then attach the clamping assembly 108, if desired. The physician can select an optimum placement of the bone pins because the clamping assembly 108 can be easily secured to the bone pins 216, regardless of their orientation, after the bone pins 216 are secured. The physician is not limited by the clamping assembly 108 when selecting locations for bone pin placement.

After the bone pins 216 are secured to the bone(s), the physician can attach the second clamp 170 of the clamping assembly 108 to a rod assembly, e.g., rod assembly 106 of FIG. 1), adjust the clamping member 176 (via the polyaxial joint 220) to align the clamping member 176 with the bone pins 216, insert the bone pins 216 into respective bone pin locking members 200, and then tighten the fixation bolt 192 to secure the bone pins 216 within the third clamp 182 and the fourth clamp 184. Alternatively, in some example implementations, the physician can first attach the clamping assembly 108 and then secure the bone pins 216 to the bone(s).

An example method of external fixation of a limb can include securing a first bone pin to the first bone portion, e.g., a portion of a tibia 222 of FIG. 1. Then, a pre-assembled external fixation system, including a rod assembly, can be attached to the first bone pin, e.g., bone pin 118A of the external fixation system 100 of FIG. 1. The physician can secure a second bone pin to a bone in a foot, e.g., bone pin 216A of FIGS. 5A, 5B. The physician can attach a clamping assembly to the rod assembly, e.g., the clamping assembly 108 of FIGS. 5A, 5B. When the clamping assembly is adjusted and/or positioned via the polyaxial joints to reach the second bone pin, the second bone pin 216A can be attached to the bone pin locking member 200A of the clamping assembly, and then the clamping assembly can be secured, e.g., the clamps tightened to prevent further adjustment or movement.

FIG. 6 is a cross-sectional view of the clamping assembly 108 of FIG. 1. As mentioned above, the second end 180 of the clamping member 176 defines a spherical portion that is configured to receive the nut 194. In the example configuration of FIG. 6, the spherical portion 190 configured to receive the nut 194 defines a tapered aperture 224. In some examples, the tapered aperture 224 can taper from a first dimension at an outer portion to a second dimension toward a center of the spherical portion, where the first dimension is larger than the second dimension.

As the fixation bolt 192 is turned, the nut 194 is pulled inward toward the center of the spherical portion 190. In some examples, to facilitate the movement of the nut 194 toward the center of the spherical portion 190, the sides of the nut 194 can be tapered to correspond to the tapered aperture 224. As the nut 194 is pulled inward toward the center of the spherical portion 190, the nut 194 causes the spherical portion 190 to expand outwardly against the first clamp 168 of the longitudinal member 162.

FIG. 7 depicts an example of a clamping strut assembly, e.g., the first clamping strut assembly 110 of FIG. 1. The clamping strut assembly 110 can include a body 154 having a first clamp 144 configured to receive an end of a rod assembly, e.g., a rod assembly 104 of FIG. 1. A first fixation bolt 146 can extend through an end of the body 154. When turned, the first fixation bolt 146 can close a gap 226 and tighten the first clamp 144, thereby securingly engaging an end of the rod assembly.

The clamping strut assembly 110 can further include a second clamp 148 having a plate 152, a second fixation bolt 228, and a nut 230 to receive the bolt 228. When the second fixation bolt 228 is tightened, the clamp 148 is configured to securingly engage one or more bone pins e.g., bone pins 150A, 150B of FIG. 1. In some examples, the bone pins 150A and 150B can be calcaneal pins. As the second fixation bolt 228 is tightened, the bone pins 150A, 150B are secured between the plate 152 and the body 154 of the first clamping strut assembly 110. In the example shown in FIG. 7, the body 154 can define grooves 232A to receive each of the bone pins 150. The plate 152 can define similar grooves 232B.

As shown and described above with respect to FIG. 1, the system 100 of FIG. 1 can include a kickstand member 114 (shown in FIG. 1). The body 154 of the clamping strut assembly 110 can include a protrusion 234 configured to mate with a corresponding recess or cavity defined by an end of the kickstand member 114. A fixation bolt 156 (shown in FIG. 1) can extend through the end of the kickstand member 114 and through the protrusion 234 of the clamping strut assembly 110.

In some examples configuration, such as in FIG. 7, the second clamp 148 of the clamping strut assembly 110 can be elevated. For example, the body 154 can include a portion 236, e.g., a sloped portion, that can position the second clamp 148 above the rest of body 154. As seen in FIG. 1, the raised position of the clamp 148 can allow the bone pins 150 to be positioned such that when the kickstand member 114 is rotated behind the patient's heel, the bone pins 150 are above the kickstand member 114 and will not interfere with its movement.

Various Notes and Examples

Example 1 includes subject matter (such as a system, apparatus, assembly) comprising: a longitudinal member having a first end and a second end, the second end defining a first clamp; a second clamp configured to attach to the first end of the longitudinal member and connect to a rod assembly; a clamping member including a first end, a second end defining a spherical portion, and a third clamp, wherein the first clamp of the longitudinal member is configured to receive the second end of the clamping member.

In Example 2, the subject matter of Example 1 can optionally include, wherein the first clamp includes a spherical clamping surface, the spherical clamping surface configured to receive the spherical portion and form a polyaxial joint between the clamping member and the longitudinal member.

In Example 3, the subject matter of one or more of Examples 1 and 2 can optionally include; wherein the spherical portion is configured to expand.

In Example 4, the subject matter of one or more of Examples 1-3 can optionally include, a first fixation bolt extending through a portion of the clamping member and the spherical portion; and a nut configured to receive an end of the first fixation bolt, wherein the spherical portion is configured to receive the nut, and wherein the spherical portion is configured to expand when the first fixation bolt is turned and the nut is pulled into the spherical portion.

In Example 5, the subject matter of Example 4 can optionally include, wherein the nut is tapered, and wherein the spherical portion configured to receive the nut defines a tapered aperture that tapers from a first dimension at an outer portion to a second dimension toward a center of the spherical portion, the first dimension larger than the second dimension.

In Example 6, the subject matter of one or more of Examples 1-5 can optionally include, wherein the third clamp is configured to contract when the first fixation bolt is turned and the nut is pulled into the spherical portion.

In Example 7, the subject matter of one or more of Examples 1-6 can optionally include, a first bone pin locking member including a spherical portion; wherein the third clamp includes a spherical clamping surface configured to receive the spherical portion of the first bone pin locking member and form a polyaxial joint between the clamping member and a first bone pin.

In Example 8, the subject matter of Example 7 can optionally include, wherein the spherical portion of the first bone pin locking member defines at least one slot.

In Example 9; the subject matter of Example 8 can optionally include, wherein the spherical portion of the first bone pin locking member is configured to compress when the third clamp contracts.

In Example 10, the subject matter of one or more of Examples 1-9 can optionally include: a second fixation bolt configured to extend through the first end of the longitudinal member and at least a portion of the second clamp, wherein the second clamp includes a U-shaped clamp.

In Example 11, the subject flatter of one or more of Examples 1-10 can optionally include, wherein the clamping member further includes a fourth clamp, wherein the fourth clamp is configured to contract when the first fixation bolt is turned and the nut is pulled into the spherical portion, the clamping assembly comprising: a second bone pin locking member including a spherical portion, wherein the fourth clamp includes a spherical clamping surface, the spherical clamping surface of the fourth clamp configured to receive the spherical portion of the second bone pin locking member and form a polyaxial joint between the clamping member and a second bone pin.

In Example 12, the subject matter of one or more of Examples 1-11 can optionally include, the first bone pin and the second bone pin.

In Example 13, the subject matter of one or more of Examples 1-12 can optionally include, the rod assembly, the rod assembly configured to secure to and extend between a first external clamp assembly and a second external clamp assembly, the rod assembly including a first tubular member and a second tubular member received in the first tubular member; wherein the second clamp configured to attach to the first end of the longitudinal member and connect to a rod assembly is configured to connect to one of the first tubular member and the second tubular member.

Example 14 includes subject matter (such as a system, apparatus, assembly) comprising a longitudinal member having a first end and a second end, the second end defining a first clamp, the first clamp including a spherical clamping surface; a U-shaped clamp configured to attach to the first end of the longitudinal member and connect to a rod assembly; a clamping member including a first end, a second end defining a spherical portion configured to expand, and a third clamp; a first fixation bolt extending through a portion of the clamping member and the spherical portion; a nut configured to receive an end of the first fixation bolt; and a first bone pin locking member including a spherical portion, wherein the first clamp of the longitudinal member is configured to receive the second end of the clamping member, wherein the spherical clamping surface of the first clamp is configured to receive the spherical portion and form a polyaxial joint between the clamping member and the longitudinal member, wherein the spherical portion is configured to expand when the first fixation bolt is turned and the nut is pulled into the spherical portion, and wherein the third clamp includes a spherical clamping surface configured to receive the spherical portion of the first bone pin locking member and form a polyaxial joint between the clamping member and a first bone pin.

Example 15 includes subject matter (such as a system, apparatus, assembly) comprising a first clamp assembly; a second clamp assembly; a rod assembly secured to and extending between the first clamp assembly and the second clamp assembly, the first rod assembly including a first tubular member and a second tubular member received in the first tubular member; and a bone pin clamping assembly comprising: a longitudinal member having a first end and a second end, the second end defining a first clamp; a second clamp configured to attach to the first end of the longitudinal member and connect to the rod assembly; a clamping member including a first end, a second end defining a spherical portion, and a third clamp, wherein the first clamp of the longitudinal member is configured to receive the second end of the clamping member.

In Example 16, the subject matter of Example 15 can optionally include, wherein the first clamp includes a spherical clamping surface, the spherical clamping surface configured to receive the spherical portion and form a polyaxial joint between the clamping member and the longitudinal member.

In Example 17, the subject matter of one or more of Examples 15-16 can optionally include; wherein the spherical portion is configured to expand.

In Example 18, the subject matter of one or more of Examples 15-17, can optionally include a first fixation bolt extending through a portion of the clamping member and the spherical portion; and a nut configured to receive an end of the first fixation bolt, wherein the spherical portion is configured to receive the nut, and wherein the spherical portion is configured to expand when the first fixation bolt is turned and the nut is pulled into the spherical portion.

In Example 19, the subject matter of Example 18 can optionally include, wherein the nut is tapered, and wherein the spherical portion configured to receive the nut defines a tapered aperture that tapers from a first dimension at an outer portion to a second dimension toward a center of the spherical portion, the first dimension larger than the second dimension.

In Example 20, the subject matter of one or more of Examples 15-19 can optionally include, wherein the third clamp is configured to contract when the first fixation bolt is turned and the nut is pulled into the spherical portion.

Example 20 can include subject matter (such as a method) for external fixation of a limb, the limb having a first bone portion, the method comprising: securing a first bone pin to the first bone portion; attaching a pre-assembled external fixation system to the first bone pin, the external fixation system comprising a rod assembly; securing a second bone pin to a bone in a foot; attaching a clamping assembly to the rod assembly, the clamping assembly comprising: a longitudinal member having a first end and a second end, the second end defining a first clamp; a second clamp configured to attach to the first end of the longitudinal member and connect to the rod assembly; a clamping member including a first end, a second end defining a spherical portion, a bone pin locking member; and a third clamp configured to receive the bone pin locking member, wherein the first clamp of the longitudinal member is configured to receive the second end of the clamping member; aligning the bone pin locking member of the clamping assembly with the second bone pin; inserting the second bone pin into the bone pin locking member of the clamping assembly; and securing the bone pin locking member of the clamping assembly to the second bone pin.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B"

includes "A but not B," "B but not A," and "A and B," unless otherwise indicated. In this document, the terms "including" and "in which" are used as the plain-English equivalents of the respective terms "comprising" and "wherein," Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along TO with the full scope of equivalents to which such claims are entitled.

The invention claimed is:

1. A clamping assembly comprising:
   a longitudinal member having a first end and a second end, the second end defining a first clamp;
   a second clamp configured to attach to the first end of the longitudinal member and connect to a rod assembly;
   a clamping member including a first end, a second end defining a spherical portion, and a third clamp;
   a first fixation bolt extending through a portion of the clamping member and the spherical portion; and
   a nut configured to receive an end of the first fixation bolt,
   wherein the first clamp of the longitudinal member is configured to receive the second end of the clamping member;
   wherein the spherical portion is configured to receive the nut, and
   wherein the spherical portion is configured to expand and the third clamp is configured to contract when the first fixation bolt is turned and the nut is pulled into the spherical portion.

2. The clamping assembly of claim 1, wherein the first clamp includes a spherical clamping surface, the spherical clamping surface configured to receive the spherical portion and form a polyaxial joint between the clamping member and the longitudinal member.

3. The clamping assembly of claim 1, wherein the nut is tapered, and wherein the spherical portion defines a tapered aperture that tapers from a first dimension at an outer portion to a second dimension toward a center of the spherical portion, the first dimension larger than the second dimension.

4. The clamping assembly of claim 1, comprising:
   a first bone pin locking member including a spherical portion,
   wherein the third clamp includes a spherical clamping surface configured to receive the spherical portion of the first bone pin locking member and form a polyaxial joint between the clamping member and a first bone pin.

5. The clamping assembly of claim 4, wherein the spherical portion of the first bone pin locking member defines at least one slot.

6. The clamping assembly of claim 4, wherein the spherical portion of the first bone pin locking member is configured to compress when the third clamp contracts.

7. The clamping assembly of claim 1, comprising:
   a second fixation bolt configured to extend through the first end of the longitudinal member and at least a portion of the second clamp,
   wherein the second clamp includes a U-shaped clamp.

8. The clamping assembly of claim 1, wherein the clamping member further includes a fourth clamp, wherein the fourth clamp is configured to contract when the first fixation bolt is turned and the nut is pulled into the spherical portion, the clamping assembly comprising:
   a second bone pin locking member including a spherical portion,
   wherein the fourth clamp includes a spherical clamping surface, the spherical clamping surface of the fourth clamp configured to receive the spherical portion of the second bone pin locking member and form a polyaxial joint between the clamping member and a second bone pin.

9. The clamping assembly of claim 1, comprising a first bone pin and a second bone pin.

10. The clamping assembly of claim 1, further comprising:
    the rod assembly, the rod assembly configured to secure to and extend between a first external clamp assembly and a second external clamp assembly, the rod assembly including a first tubular member and a second tubular member received in the first tubular member,
    wherein the second clamp configured to attach to the first end of the longitudinal member and is configured to connect to one of the first tubular member and the second tubular member.

11. The clamping assembly of claim 1, wherein the third clamp includes an adjustable gap, and wherein when the first fixation bolt is turned, the adjustable gap is reduced.

12. The clamping assembly of claim 1, wherein the third clamp includes an adjustable gap, and wherein a first fixation bolt extends across the adjustable gap.

13. A clamping assembly comprising:
    a longitudinal member having a first end and a second end, the second end defining a first clamp;
    a second clamp configured to attach to the first end of the longitudinal member and connect to a rod assembly;
    a clamping member including a first end, a second end defining a spherical portion, a third clamp and a fourth clamp;
    a first fixation bolt extending through a portion of the clamping member and the spherical portion; and
    a nut configured to receive an end of the first fixation bolt,
    wherein the first clamp of the longitudinal member is configured to receive the second end of the clamping member;
    wherein the spherical portion is configured to receive the nut, and wherein the spherical portion is configured to expand and the third clamp is configured to contract when the first fixation bolt is turned and the nut is pulled into the spherical portion.

14. The clamping assembly of claim 13, wherein the first clamp includes a spherical clamping surface, the spherical clamping surface configured to receive the spherical portion and form a polyaxial joint between the clamping member and the longitudinal member.

15. The clamping assembly of claim 13, wherein the nut is tapered, and wherein the spherical portion defines a tapered aperture that tapers from a first dimension at an outer portion to a second dimension toward a center of the spherical portion, the first dimension larger than the second dimension.

16. The clamping assembly of claim 13, wherein the fourth clamp is configured to contract when the first fixation bolt is turned and the nut is pulled into the spherical portion.

17. The clamping assembly of claim 13, comprising:
a bone pin locking member including a spherical portion,
wherein the third clamp includes a spherical clamping surface configured to receive the spherical portion of the bone pin locking member and form a polyaxial joint between the clamping member and a bone pin.

18. The clamping assembly of claim 13, comprising:
a bone pin locking member including a spherical portion,
wherein the fourth clamp includes a spherical clamping surface, the spherical clamping surface of the fourth clamp is configured to receive the spherical portion of the bone pin locking member and form a polyaxial joint between the clamping member and a bone pin.

19. A clamping assembly comprising:
a longitudinal member having a first end and a second end, the second end defining a first clamp;
a second clamp configured to attach to the first end of the longitudinal member and connect to a rod assembly;
a clamping member including a first end, a second end defining a spherical portion, a third clamp, and a fourth clamp;
a bone pin locking member including a second spherical portion;
a first fixation bolt extending through a portion of the clamping member and the spherical portion; and
a nut configured to receive an end of the first fixation bolt,
wherein the first clamp of the longitudinal member is configured to receive the second end of the clamping member,
wherein the fourth clamp is configured to contract when the first fixation bolt is turned and the nut is pulled into the spherical portion, and
wherein the fourth clamp includes a spherical clamping surface, the spherical clamping surface of the fourth clamp configured to receive the second spherical portion of the bone pin locking member and form a polyaxial joint between the clamping member and a bone pin.

* * * * *